US009615600B2

(12) United States Patent
Thiede et al.

(10) Patent No.: US 9,615,600 B2
(45) Date of Patent: Apr. 11, 2017

(54) DIETETIC OR PHARMACEUTICAL PREPARATION CONTAINING TARTARY BUCKWHEAT

(75) Inventors: Hans-Michael Thiede, Potsdam (DE); Wolfgang Kehr, Berlin (DE)

(73) Assignee: THANARES GMBH, Potsdam (DE)

( * ) Notice: Subject to any disclaimer, the term of this patent is extended or adjusted under 35 U.S.C. 154(b) by 201 days.

(21) Appl. No.: 13/985,984

(22) PCT Filed: Jan. 27, 2012

(86) PCT No.: PCT/DE2012/000062
§ 371 (c)(1), (2), (4) Date: Oct. 22, 2013

(87) PCT Pub. No.: WO2012/110017
PCT Pub. Date: Aug. 23, 2012

(65) Prior Publication Data

US 2014/0044808 A1 Feb. 13, 2014

(30) Foreign Application Priority Data

Feb. 16, 2011 (DE) ........................ 10 2011 011 402
Jun. 20, 2011 (DE) ........................ 10 2011 105 406

(51) Int. Cl.

| | |
|---|---|
| ***A61K 35/20*** | (2006.01) |
| ***A61K 36/70*** | (2006.01) |
| ***A61K 36/36*** | (2006.01) |
| ***A23L 1/30*** | (2006.01) |
| ***A61K 31/7048*** | (2006.01) |
| ***A61K 45/06*** | (2006.01) |
| ***A23L 5/00*** | (2016.01) |
| ***A23L 33/105*** | (2016.01) |

(52) U.S. Cl.
CPC ............... *A23L 1/3002* (2013.01); *A23L 5/00* (2016.08); *A23L 33/105* (2016.08); *A61K 31/7048* (2013.01); *A61K 35/20* (2013.01); *A61K 36/70* (2013.01); *A61K 45/06* (2013.01)

(58) Field of Classification Search
None
See application file for complete search history.

(56) References Cited

FOREIGN PATENT DOCUMENTS

| | | | |
|---|---|---|---|
| CN | 101810276 | | 8/2010 |
| JP | 2002101833 | | 4/2002 |
| JP | 05123123 A | * | 5/2013 |
| WO | 00/15237 | | 3/2000 |

OTHER PUBLICATIONS

Zheng (XP-002679858, Oct. 19, 2009, see abstract pp. 1-2).*
Viable Herbal Solutions (see cited website of www.web.arcive.org/web/@0000124113842/http://viable-herbal.com/herbology1/herbs42, copyrighted 1996-2000, pp. 1-3).*
Zeller, et al. Buchweizen—die vergessene Kulturpflanze, Biol. Urserer Zeit, No. 1, 2004, p. 27 (translation attached).
G. Gläβer, "Comparison of antioxidative capacities and inhibitory effects on cholesterol biosynthesis of quercetin and potential metabolites" Phytomedicine 9: 33-40, 2002.

* cited by examiner

*Primary Examiner* — Chris R Tate
*Assistant Examiner* — Randall Winston
(74) *Attorney, Agent, or Firm* — Ann Wieczorek; Mayer & Williams PC

(57) ABSTRACT

The invention relates to a method for preparing a dietetic or pharmaceutical composition, comprising the following steps: a) a preparation containing rutin, in particular ground tatary buckwheat, is mixed with a protein solution in a weight ratio protein solution/buckwheat from 1 to 100 (or vice versa), wherein before the addition of buckwheat, the protein solution has been heated above room temperature, b) the mixture from step a) is held for a period of at least 10 to 1,000 s at a temperature >50° C., and c) subsequently to step b), the mixture is cooled down to a temperature below 45° C. The invention further relates to thus obtainable preparations and to the uses thereof.

7 Claims, No Drawings

DIETETIC OR PHARMACEUTICAL PREPARATION CONTAINING TARTARY BUCKWHEAT

FIELD OF THE INVENTION

The invention relates to a method for preparing a composition containing ground buckwheat and milk, to a composition obtainable by this method, and to uses thereof.

PRIOR ART AND BACKGROUND OF THE INVENTION 4-methyl catechol (4-MC) is an endogenous compound occurring in very small concentrations in the human organism, and little is known about the location of formation and regulation of the metabolism in human tissue. It is known, however, that 4-MC may be formed as a metabolite of orally ingested flavonoids such as quercetin and rutin by the activity of the intestinal microbiome in the large intestine of humans.

In vitro investigations and animal studies have described effects of 4-MC that suggest a preventive and/or therapeutic effect for humans. In the following, the different effects and therapeutic applications respectively derived therefrom are described:

1. Anti-inflammatory effects
2. Peroxyl radical and superoxide anion radical scavenging
3 Stimulation of the neurotrophins "Nerve Growth Factor" (NGF), "Brain Derived Nerve Growth Factor" (BDNF), Glial Derived Nerve Growth Factor (GDNF) and others
4 Inhibition of the cholesterol biosynthesis
5 Inhibition of the lipoxygenase
6 Stimulation of the heme oxygenase
7 Inhibition of the "angiotensin converting enzyme" (ACE) activity Specific cascade dependencies between these different effects have been described. 4-MC stimulates the phosphoinositol-3-kinase/AKT signal transduction pathway and thereby activates the expression of heme oxygenase, which in turn, also in response to oxidative stress, increases, in addition to iron, the formation of bilirubin and carbon monoxide, which in turn stimulate the expression of the neurotrophins BDNF and GDNF in neurons as well as glial cells (Furukawa, Y. et al., Biomedical Research 2010, 31:45-52; Hung, S. Y. et al., Neuropharmacology 2010 February, 58:321-329).

All effects described above are significant in view of a neuroprotective context and emphasize the role and importance of the intestinal microbial activity.

Peripheral and Autonomic Neuropathies:

To the deuteropathies of diabetes mellitus belongs the diabetic neuropathy, of which 30-50% of the diabetics are affected, and which is thus the most common peripheral neuropathy in the Western countries (Pittenger G., Vinik A., Exp Diabesity Res. 2003 October-December, 4(4):277-85 Review). As a disorder of the peripheral nervous system, it relates to both sensory and motor nerves, and by the heterogeneity, besides the thickly myelinated fibers, also the thinly myelinated fibers are affected. A greatly feared complication being strongly harmful for those affected is the so-called "diabetic foot" (diabetic podopathy). Sensory disorders with and without blood flow disorders will often result in a clinical picture leading to an amputation of the lower limb. Every year in Germany alone, about 30,000 amputations of the lower limb are performed due to this diagnosis (Chantelau E., Deutsches Ärzteblatt 2002, 99:A 2052-2056).

From animal studies on streptozotocin-treated diabetic rats, it is known that the expression of neurotrophins (nerve growth factors) such as "glial cell derived neurotrophic factor" (GDNF), neurotrophin 3, and NGF in the intestines is reduced. This is used to explain the known gastrointestinal complications in diabetic patients (Liu, W. et al., Auton Neurosci. 2010, 154:79-83).

Since the early nineties, it is known that there are a number of compounds that are able to stimulate the endogenous generation of neutrophins (Furukawa Y., et al., Biochem Pharmacol 1990 November 75, 40(10):2337-42). These substances include the alkyl catechols and in particular the 4-MC. For 4-MC it has been shown that neuropathies in various animal models (neuropathies induced by resiniferatoxin, pyridoxine, acrylamide and cytostatics as well as diabetic neuropathy induced by streptozotocin) are favorably influenced by the administration of 4-MC (Hanaoka Y., et al., J Neurol Sci. 1994 March; 122(1):28-32). Similarly, the gentamicin-induced ototoxicity is antagonized by 4-MC via stimulation of NGF and other neurotrophins.

Also in the "crush injury" model of the sciatic nerves of the mouse, MC-4 enhanced the reinnervation of the cutaneous nerves, in particular the non-myelinated nerve fibers (Hsieh, Y. L. et al., J Neuropathol Exp Neurol. 2009; 68:1269-1287).

These results suggest that also in humans, alkyl catechols and their derivatives have preventive and therapeutic effects on various types of neuropathies, as in diabetic neuropathy, but also in
neuropathy induced by chemotherapy, and
neuropathy as a result of chronic alcohol abuse.

Central Nervous Degenerative Diseases:

In Germany alone, currently more than a million people suffer from dementia, about 700,000 thereof from Alzheimer's disease, a neurodegenerative disease. Every year, approximately 200,000 new dementia diseases are diagnosed, of which about 120,000 are the Alzheimer's type. From Parkinson's disease suffer in Germany currently 300,000-400,000. Due to the demographic trends, the prevalence of both diseases will increase. The financial burdens of the health system caused by these diseases are very high—the treatment and care costs of an Alzheimer's patient today are around € 40,000 per year—and will continue to rise. Therapeutic agents for the symptomatic treatment of Parkinson's disease are indeed already available today, and the first products to improve the cognitive functions in patients with Alzheimer's disease show marginal effects, a real breakthrough with agents that stop the progression of these neurodegenerative diseases could however so far not be achieved, despite intensive worldwide research.

The effects of the alkyl catechols and their metabolites indicate a significant therapeutic potential: Besides the already mentioned stimulation of neurotrophins, which also takes place in the central nervous system and counteracts the neurodegeneration process, signal transduction effects have been described, suggesting that by activation of heme oxygenase-1 expression, 4-MC has neuroprotective effects, in particular against the harmful oxidative stress (Furukawa, Y. et al., Biomedical Res 2010, 31:45-52). MC-4 further stimulates the mitogen-activated protein kinase (MAPK/ERK1/2), which in turn activates the "cAMPresponse element binding protein" (CREB). CREB plays an important role for the nerve growth as well as for the survival of the nerve cells.

Oxidative stress is associated with the death of nerve cells and plays a major role in the pathogenesis of many chronic degenerative diseases such as Alzheimer's, Parkinson's, Huntington's chorea and the amyotrophic lateral sclerosis. A signal transduction pathway, in which the transcriptional activation of protective genes is mediated by a "cis-acting element", the so-called "anti-oxidant responsive element" (ARE), has an increasing importance. Activation by the transcription factor NF-E2-related factor 2 (Nrf2), which binds to ARE, protects nerve cells against cell death induced by oxidative stress (Johnson, J. A., et al., Ann NY Acad. Sci. 2008; 1147:61-69). 4-MC activates Nrf2 and can also act in a neuroprotective manner via this signal transduction pathway (Satoh, T., et al. Biochem Biophys Res Commun. 2009; 379:537-341).

Alkyl catechols such as 4-MC and/or 3,4-dihydroxyphenylacetic acid (another metabolite of rutin) have additional anti-inflammatory properties, which manifest in the inhibition of the expression of the inducible NO synthase and the inhibition of the release of proinflammatory cytokines such as TNF from microglia, therewith clear neuroprotective effects being associated (Zheng, L. T. et al., Eur J Phormacol 2008; 588:106-113). These protective effects can be used to treat neurodegenerative diseases that are associated with marked activation of the microglia.

Maintaining or improving cognitive functions is of great importance for demented patients, e.g. patients with Alzheimer's disease. Indications that alkyl catechols have a positive impact on cognitive performance, result from investigations by Sun, M. K. et al., Neuroreport. 2008; 19:355-359). After intraventricular administration, 4-MC also improved the spatial learning and memory of rats, an effect where apparently BDNF is involved, as simultaneous administration of BDNF antibodies suppressed the effect of 4-MC.

O-methyl metabolites of alkyl catechols, too, such as 2-methoxy-4-ethylphenol have neuroprotective effects that can therapeutically be used in the treatment of degenerative diseases of the central nervous system. They protect nerve cells—as has been shown for hippocampal neurons—against the excessive, neurotoxic influx of calcium ions mediated by NMDA receptors (Fukumori R. et al., J Pharmacol Sci. 2010; 112:273-281).

Hypertension/Atherosclerosis:

In vitro studies on liver cells indicate that not only quercetin, but also 4-MC inhibits the hepatocellular cholesterol synthesis in the μmol region (Glasser G. et al., Phytomedicine 2002, 9:33-40). The inhibition of the angiotensin converting enzyme and other metallopeptidases is described in Bormann, H., et al., Pharmacy. 2000, 55: 129-132.

Diabetes Mellitus:

Inhibition of non-oxidative AGE (advanced glycation end product) formation by 4-MC and DOPAC was shown in Pashikanti, S. et al., Free Radic Biol Med. 2009 Dec. 4.

Osteoporosis:

Metabolites of alkyl catechols such as 2-methoxy-4-methyl phenol (creosol) and 2-methoxy-4-ethylphenol, generated by the catalytic action of catechol-O-methyltransferase, prevent the osteoporosis occurring after ovariectomy of mice—an experimental model of the post-menopausal osteoporosis—probably by inhibition of bone-degrading osteoclasts in conjunction with an anti-oxidative effect on osteoblasts promoting bone growth (Moriguchi N., et al., Biochem Pharmacol 2007, 73:385-393). For hydroxytyrosol (3,4-dihydroxyphenyl-ethanol), too, an appropriate bone-protective effect in ovariectomized rats has been described (Puel C. et al. J Agric Food Chem. 2008; 56: 9417-9422).

Preparations containing ground buckwheat and milk are well known as foods from the practice and from the document JP 2008 271 811 A.

According to this document, buckwheat grains are first subjected to a thermal steam treatment. The milk is not heated before admixture of the buckwheat. From the document Zeller, F. J., et al., Biol. Unserer Zeit, 34th issue 2004, No. 1, pp. 24 ff, it is known to mix normal buckwheat with diluted and heated milk.

TECHNICAL OBJECT OF THE INVENTION

It is the technical object of the invention to provide a dietary composition and a method for preparing the same, which provides high levels of 4-MC in the organism.

BASICS OF THE INVENTION AND PREFERRED EMBODIMENTS

In order to achieve this technical object, the invention teaches a method for preparing a dietetic or pharmaceutical composition, comprising the steps: a) ground tatary buckwheat is mixed with an aqueous protein solution in a weight ratio protein solution/buckwheat from 1 or 2 to 100 (or vice versa), wherein before the addition of buckwheat, the protein solution has been heated above room temperature, b) the mixture from step a) is brought for a period of at least 10 to 1,000 s to a temperature >50° C., and held at this temperature, and c) subsequently to step b), the mixture is cooled down to a temperature below 45° C. The range of the weight ratio protein solution/buckwheat from 1 (or 2) to 100 means that at the lower limit of the range, one part by weight buckwheat is mixed with one part by weight (or 2) protein solution, while at the upper limit of the range, one part by weight buckwheat is mixed with 100 parts by weight of protein solution. The same applies in reverse.

The ground tatary buckwheat used needs not be subjected to a pre-treatment, in particular it is not necessary to subject buckwheat grains to a steam treatment.

Compared to the mixture of the tatary buckwheat with cold milk or with such at room temperature, the procedure according to the invention is advantageous in that a reaction of rutin to quercetin does not or hardly take place due to the thermal inactivation of the corresponding enzymes, and a bitter taste is avoided.

The invention is based on the finding that surprisingly, the quantity of 4-MC available in the organism, formed primarily from rutin contained in the tatary buckwheat, is particularly high, if the preparation is produced with boiled hot protein solution or by boiling the mixture of buckwheat and the protein solution, compared with the use of water or cold protein solution and without heating.

The advantages of the invention are however also obtained with the following process variants.

Firstly, by a method for preparing a dietetic or pharmaceutical composition, comprising the following steps: a) ground tatary buckwheat is mixed with water in a weight ratio water/buckwheat from 1 or 2 to 100 (or vice versa), wherein before the addition of buckwheat, the water has been heated above room temperature, b) the mixture from step a) is brought for a period of at least 10 to 1,000 s to a temperature >50° C., and held at this temperature, c) subsequently to step b), the mixture is cooled down to a temperature below 50° C., and d) subsequently to step c), a protein solution is added, in a weight ratio protein solution/mixture from 1:10 to 10:1, preferably 1:10 to 2:1. The product obtained may then be dried or lyophilized. The range of the weight ratio protein solution/buckwheat from 1 (or 2) to 100 means that at the lower limit of the range, one part by weight buckwheat is mixed with one part by weight (or 2) protein solution, while at the upper limit of the range, one part by weight buckwheat is mixed with 100 parts by weight of protein solution. The same applies in reverse.

Secondly, by a method for preparing a dietetic or pharmaceutical composition, comprising the following steps: a) ground tatary buckwheat is mixed with an organic solvent (extracting agent), preferably a C1 to C8 alkanol, in particular methanol, ethanol, acetone or ethyl acetate, or mixtures thereof or mixtures of one or more of such solvents with water, with an aqueous content from 5 to 60 vol-%, in particular 10 to 40 vol-%, in a weight ratio buckwheat/solvent from 1 or 2 to 100 (or vice versa), wherein before the addition of buckwheat, the solvent has been heated above room temperature, b) the mixture from step a) is brought for a period of at least 10 to 1,000 s to a temperature >50° C., preferably to the boiling point of the solvent or up to 10 or 20° C. below the boiling point, and held at this temperature, c) subsequently to step b), the mixture is cooled down to a temperature below 45° C., d) immediately before, during or after step c), the obtained solution is concentrated, preferably to a residual content of less than 10 wt-%, more preferably less than 5 wt-%, referred to the quantity of solvent, e) optionally, subsequently a protein solution (protein solution at room temperature or heated, in particular to 50 to 90° C.) is added, f) further optionally, the product obtained in step d) or e) is dried or lyophilized. The range of the weight ratio solvent/buckwheat from 1 (or 2) to 100 means that at the lower limit of the range, one part by weight buckwheat is mixed with one part by weight (or 2) solvent, while at the upper limit of the range, one part by weight buckwheat is mixed with 100 parts by weight of solvent. The same applies in reverse. With respect to the optional step e), it is to be noted that the added quantity (parts by weight) of protein solution referred to the solution from step d) may be between 1:50 and 50:1. It is of course also possible to dry/lyophilize the product from step d) without the addition of protein solution and to add dried/lyophilized protein solution in the above proportions to the product from step d).

Thirdly, by a method for preparing a dietary or pharmaceutical composition, comprising the following steps: a) ground tatary buckwheat is mixed with an organic solvent, preferably a C1 to C8 alkanol, in particular methanol, ethanol, acetone or ethyl acetate, or mixtures thereof or mixtures of one or more of such solvents with water, with an aqueous content from 5 to 60 vol-%, in particular 10 to 40 vol-%, in a weight ratio buckwheat/solvent from 1 or 2 to 100 (or vice versa), wherein before the addition of buckwheat, the solvent is at room temperature, b) the mixture from step a) is adjusted by adding an organic or inorganic acid or acid solution to a pH below 1.5, without heating the mixture, and is held at this pH for a period of at least 1 s, preferably at least 100 s (the organic acids may for instance be acetic acid, preferably of >10%, or formic acid, preferably of >5%. The inorganic acid may for instance be HCl, in particular 0.05 to 0.5 N HCl, preferably 0.05 to 0.2 N HCl, for instance 0.1 N HCl), c) immediately before, during or after step b), the obtained solution is concentrated, preferably to a residual content of less than 10 wt-%, more preferably less than 5 wt-%, referred to the quantity of solvent, d) optionally, subsequently a protein solution (protein solution at room temperature or heated, in particular to 50 to 90° C.) is added, e) further optionally, the product obtained in step c) or d) is dried or lyophilized. With respect to the optional step d), it is to be noted that the added quantity (parts by weight) of protein solution referred to the solution from step c) may be between 1:50 and 50:1. It is of course also possible to dry/lyophilize the product from step c) without the addition of protein solution and to add dried/lyophilized protein solution in the above proportions to the product from step e). Before step c), optionally a neutralization with a physiologically acceptable organic or inorganic base, to pH 5 to 9, in particular 6 to 8 may take place. The range of the weight ratio protein solution/buckwheat from 1 (or 2) to 100 means that at the lower limit of the range, one part by weight buckwheat is mixed with one part by weight (or 2) protein solution, while at the upper limit of the range, one part by weight buckwheat is mixed with 100 parts by weight of protein solution. The same applies in reverse.

Fourthly, by a method for preparing a dietary or pharmaceutical composition, comprising the following steps: a) ground tatary buckwheat is mixed with water in a weight ratio solvent/buckwheat from 1 or 2 to 100 (or vice versa), wherein before the addition of buckwheat, the water is at room temperature, b) the water added in step a) or the mixture from step a) is reacted with a salt of one or more of the elements Mg, Cu, or Fe without heating the mixture or the water (if the water added in step a) is reacted with the salt, it may, of course, be heated to improve the dissolving of the salt and be cooled before the addition in step a)), c) the mixture from step b) is optionally subjected after 0.1 to 100 min, preferably 0.1 to 10 min to a separation of the salt or salts, d) optionally, subsequently a protein solution (protein solution at room temperature or heated, in particular to 50 to 90° C.) is added, e) further optionally, the product obtained in step c) or d) is dried or lyophilized. With respect to the optional step d), it is to be noted that the added quantity (parts by weight) of protein solution referred to the solution from step c) (with or without salt) may be between 1:50 and 50:1. It is of course also possible to dry/lyophilize the product from step c) without the addition of protein solution and to add dried/lyophilized protein solution in the above proportions to the product from step e). Salts may for example be $MgCl_2$, $CuCl_2$, or $FeCl_2$. The salt concentrations may be in the range from 0.005 to 0.5 mol/l, $MgCl_2$ in particular 0.05 mol/l, $CuCl_2$ in particular 0.02 mol/l, and $FeCl_2$ in particular 0.1 mol/l. The range of the weight ratio protein solution/buckwheat from 1 (or 2) to 100 means that at the lower limit of the range, one part by weight buckwheat is mixed with one part by weight (or 2) protein solution, while at the upper limit of the range, one part by weight buckwheat is mixed with 100 parts by weight of protein solution. The same applies in reverse. While in this variant, heating of the solvent is not necessary, because of the addition of the salt, the solvent or the mixture solvent/buckwheat may however of course also (additionally) be heated, in an analogous manner to the other variants described above. The variant described here has the advantage that such a heating is not necessary for disabling unwanted enzyme activities.

All methods according to the invention are based on the underlying concept to inactivate endogenous enzymes contained in the tatary buckwheat, so that a very high yield of 4-MC can be achieved.

In all the foregoing and the following variants of the method according to the invention, the mixture can in any of the process steps, independently of the other process steps, be either not agitated or agitated, in particular stirred, for a period from 0.1 to 200 min, in particular 1 to 60 min. The term room temperature, unless other suitable ranges are given above or below, refers to a temperature in the range from 15 to 25° C., for example 20° C. For all process variants, the following additional considerations apply in a corresponding or applicable manner. The same applies to uses or further processings and products containing a product of one of the processes.

It is common to all described procedures that in place of the tatary buckwheat, any other preparation containing rutin may also be used. The rutin may be present in an aqueous solution, as well as in an alcoholic solution or in a mixture of alcohol and water. Suitable alcohols are the compounds mentioned elsewhere. The composition containing rutin may be of natural origin, for example as a product of an extraction from a plant species naturally containing rutin. But it may however also be synthetic, for example by addition of the rutin to the used aqueous or organic solvent, and other substances may further be added, if necessary. The quantity of rutin in the preparation may be in the range from 1 g rutin in 5 ml solvent up to 1 g rutin in 200 ml. Preferably, the range is 1 g rutin in 10 ml to 50 ml, for example 1 g rutin in 20 ml solvent.

The following definitions and embodiments are equally applicable to all above variants of the invention.

The term protein solution refers to mixtures of water and proteins, wherein the proteins may be dissolved or suspended in the aqueous phase. An appropriate protein solution according to the invention generally, but not necessarily, has a protein content from 0.1 to 20 wt-%, particularly 1 to 5 wt-%, preferably 2 to 4 wt-% protein, referred to the quantity of used protein solution. The determination of the protein content can be carried out in particular by means of Kjeldahl methods standardized in the food industry, in particular the dairy industry, and a factor 6.25 is selected for determining the protein content from the nitrogen content of a sample, i.e., the weight proportion of nitrogen is multiplied by 6.25 and then yields the weight proportion of protein in the protein solution.

Tartary buckwheat is also known as duckwheat. The binomial name is *Fagopyrum tataricum*. A subspecies is *tataricum Fagopyrum* spp. *potanini*. Tatary Buckwheat is characterized, compared to other types of buckwheat, by a relatively high content of rutin (see also Zeller, F. J., Die Bodenkultur, 52(3):259 ff (2001).

The term ground buckwheat includes, as ground products, flour (particle size<180 μm, measured and fractionated by sieving), coarse-grained flour (80 to 300 μm), semolina (300 to 1,000 μm) and groats (>1,000 μm), each individually or in any combination with each other. In this specification, the term "buckwheat" is in particular used as a synonym for buckwheat seeds.

The weight ratio protein solution/buckwheat is preferably 4 to 20. The range of the weight ratio protein solution/buckwheat 4 to 20 means that at the lower limit of the range, one part by weight buckwheat is mixed with 4 parts by weight of protein solution, while at the upper limit of the range, the mixture is one part by weight buckwheat mixed with 20 parts by weight of protein solution. The same applies in reverse. The room temperature is typically in the range from 5 to 40° C. In particular, it is 15 to 25° C., for example 20° C.

As a protein solution, in principle any milk intended for human or animal consumption in food and prepared by a conventional food processing technology can be used. The protein solution is for example selected from the group consisting of milk of cows, buttermilk, milk of camels, milk of mares, milk of goats, milk of donkeys, milk of llamas, milk of reindeers, milk of water buffaloes and milk of sheep. However, protein solutions of plant origin can also be used, such as soy milk or coconut milk. The protein solution may also be made with a milk powder obtained from one or more of the above mentioned types of milk, by mixing with water. For certain applications, such as for persons with lactose intolerance or for use in animals, it may be provided that the protein solution or milk is lactose-free. Because of the availability and low price, milk of cows is preferred. When the protein solution is a milk, it typically has a fat content from 0.5 to 8%, in particular 1.3 to 6%. It may be untreated, pasteurized, subjected to an extended shelf life (ESL) process, or UHT milk. Such treatment methods are well known to the man skilled in the art of food technology and need not further be described here.

In a preferred variant of the invention, before the addition of buckwheat, the protein solution is heated to a temperature of at least 50° C. or 60° C., in particular at least 80° C., preferably at least 90° C., and held at this temperature until the buckwheat is added.

In step b), the mixture is heated in any case to a temperature of preferably at least 60° C., in particular at least 80° C., preferably at least 90° C., or held at this temperature.

In step c), the mixture is preferably cooled down to a temperature from 5 to 40° C., in particular 8 to 30° C.

The preparation thus obtained is as such suitable for direct human or animal consumption. However, for other applications it is preferred that after step c) or the final stage described above of a variant of the invention, a drying process, in particular a freeze-drying process (lyophilization) of the preparation is carried out. The term drying means the removal of water so to obtain a residual water content of less than 5 wt-%, preferably less than 2 wt-%, referred to the total weight of the dried composition. In principle, however, other drying methods, such as spray-drying, may also be used.

However, it is also possible to submit the mixture to usual food technological methods for further processing after the respective final process step of the above different variants of the invention, for example the further processing to yoghurt, kefir, cheese, or whey.

The invention also relates to a dietary or pharmaceutical preparation obtained by one of the above methods according to the invention. Typically, it contains 0.5 to 10 wt-%, in particular 1 to 5 wt-%, preferably 2 to 4 wt-% rutin, the figures being referred to the quantity of used buckwheat seeds. In absolute amounts, a unit of administration contains at least 0.1 g rutin, preferably at least 0.5 g, in particular at least 1.0 g, and with respect to the determination of the amounts or proportions, reference is made to the following paragraph. Further may be contained food additives, preferably selected from the group consisting of food dyes, preservatives, vitamins and minerals and/or galenic excipients. By way of example only, the preparation, in a lyophilized variant, may be encapsulated in a capsule being usual for the pharmaceutical industry.

The invention also relates to a use of a preparation according to the invention for preparing a functional food, wherein a physiologically effective quantity of the preparation is added to the food. A physiologically effective quantity is, for example, a quantity containing at least 0.1 g rutin, preferably at least 0.5 g, most preferably at least 1.0 g. The quantity of rutin is determined by measuring the content of rutin in the buckwheat used. An exemplary method of determination is described in Gierlowska J., et al., Food/Nahrung Vol. 2, issue 7, 705-709 (1958). Generally all the usual methods with extraction of the buckwheat by means of for instance hot water or methanol and analysis with column chromatographic methods can be used. The invention also includes a functional food available in the above manner.

Furthermore, the invention also comprises the use of a preparation according to the invention or a functional food according to the invention for preparing a composition for the treatment or prophylaxis of a disease from the group comprising peripheral and autonomic neuropathy, central nervous system degenerative diseases, hypertension, atherosclerosis, venous insufficiency, diabetes mellitus, osteoporosis, cataracts, and photoaging of the skin.

Finally, the invention comprises a method for increasing the bioavailability of an alkyl catechol, in particular of 4-MC and/or 3,4-dihydroxyphenylacetic acid, in an organism, in particular an animal or human organism, wherein a preparation according to the invention or a functional food is administered to the organism in a physiologically effective dose, in particular is administered orally or for consumption.

Formulations according to the invention cannot only be used in human medicine, but also in veterinary medicine. Then it will in most cases be recommendable to use a lactose-free variant of the invention.

In the following the invention is explained in more detail with reference to non-limiting examples.

After oral administration, rutin itself is not absorbed from the intestine into the blood circulation. Initially, rutin is metabolized in the colon by the gut flora present there to quercetin-3-glucoside and quercetin, which partially goes over into the blood or is converted in the intestinal mucosa, but also in the liver into quercetin conjugates. The remaining part of the quercetin is further metabolized in the colon by the microbiome. The main metabolites are 3,4-dihydroxyphenylacetic acid and 4-MC.

A large part of the health-promoting effects of rutin are attributed to the 4-MC (see introduction). It was therefore desirable to reliably increase the "bioavailability" of 4-MC.

As a measure of the "bioavailability", the total excretion of 4-MC in the urine of healthy probands after administration of various preparations of tataric of buckwheat was used.

From the Table results that after eating warm mash made from 75 g ground buckwheat, with 500 ml boiling water having been added before, the renal total excretion of 4-MC is in a range comparable to the total excretion of 4-MC after oral administration of 2 g rutin in hot milk. (The quantity of rutin contained in 75 g ground buckwheat corresponds to approx. 2 g rutin).

Surprisingly, the renal total excretion of 4-MC, after eating warm mash made from 75 g ground buckwheat, to which previously 500 ml boiling milk had been added, was 3 times above the excretion after consumption of the corresponding above preparation with boiling water.

TABLE

Preparation of buckwheat with milk: Renal excretion of 4-methylcatechol (4-MC), dihydroxyphenylacetic acid (DOPAC), and quercetin in healthy probands; urine collection period 0 to 48 hours.

| Preparation | 4-MC, mg total excretion | DOPAC, mg total excretion | Quercetin, mg total excretion |
|---|---|---|---|
| 75 g tat. buckwheat in 500 ml boiled water | 7.33 | 14.72 | 3.33 |
| 40 g tat. buckwheat in 400 ml cold milk (X 1.875, i.e., corresponding to 75 g buckwheat) | 5.43 (10.2) | 5.16 (9.67) | |
| 75 g tat. buckwheat in 400 ml cold and then boiled-up milk | 19.3 | 11.23 | 15.64 |
| 75 g tat. buckwheat in 500 ml boiling milk | 23.5 | 15.49 | 3.57 |
| For comparison: 2 g rutin in 500 ml hot milk | 6.0 | 6.53 | |

The invention claimed is:

1. A method for preparing a dietetic or pharmaceutical composition comprising the following steps:

a) mixing ground tatary buckwheat with a protein solution in a weight ratio protein solution/buckwheat from 4 to 20, wherein before the addition of buckwheat, the protein solution has been heated to at least 60° C. and is held at this temperature until the buckwheat is added;

b) holding the mixture from step a) for a period of at least 10 to 1,000 s at a temperature of at least 80° C.; and c) subsequently to step b), cooling the mixture down to a temperature below 45° C.;

wherein the protein solution is selected from the group consisting milk of cows, buttermilk, milk of camels, milk of mares, milk of goats, milk of donkeys, milk of llamas, milk of reindeers, milk of water buffaloes, milk of sheep, soy milk, coconut milk, and lactose-free milks thereof.

2. The method according to claim 1, wherein the protein solution has a fat content from 0.5 to 8%, in particular 1.3 to 6%.

3. The method according to claim 1, wherein the protein solution is untreated, pasteurized, subjected to an extended shelf life (ESL) process, or is UHT.

4. The method according to claim 1, wherein before the addition of buckwheat, the protein solution is brought to a temperature of at least 70° C., in particular at least 80° C., preferably at least 90° C., and is held at this temperature until the buckwheat is added.

5. The method according to claim 1, wherein in step b) the mixture is brought to a temperature of at least 90° C., and is held at this temperature.

6. The method according to claim 1, wherein in step c) the mixture is cooled down to a temperature of 5 to 40° C., in particular 8 to 30° C.

7. The method according to claim 1, wherein after step c), the preparation is dried.

* * * * *